(12) United States Patent
L'Europa

(10) Patent No.: US 8,889,157 B1
(45) Date of Patent: *Nov. 18, 2014

(54) COMPOSITION FOR CARDIOVASCULAR TREATMENT

(76) Inventor: Gary L'Europa, Warwick, RI (US)

( * ) Notice: Subject to any disclaimer, the term of this patent is extended or adjusted under 35 U.S.C. 154(b) by 24 days.

This patent is subject to a terminal disclaimer.

(21) Appl. No.: 12/871,957

(22) Filed: Aug. 31, 2010

(51) Int. Cl.
*A61K 9/00* (2006.01)
*A61K 31/122* (2006.01)
*A61K 9/12* (2006.01)

(52) U.S. Cl.
USPC .............................. 424/400; 424/94.1; 424/43

(58) Field of Classification Search
USPC .......................................... 424/400, 94.1, 43
See application file for complete search history.

(56) References Cited

U.S. PATENT DOCUMENTS

| | | | |
|---|---|---|---|
| 5,770,215 A * | 6/1998 | Moshyedi | 424/440 |
| 5,948,443 A | 9/1999 | Riley et al. | |
| 5,998,448 A | 12/1999 | Lesur et al. | |
| 6,274,170 B1 * | 8/2001 | Heibel et al. | 424/458 |
| 6,365,176 B1 | 4/2002 | Bell et al. | |
| 6,465,517 B1 | 10/2002 | Van Der Zee | |
| 6,914,073 B2 | 7/2005 | Boulos et al. | |
| 6,953,593 B2 | 10/2005 | Kuhrts | |
| 7,202,229 B1 | 4/2007 | Finkelstein | |
| 2004/0018251 A1 * | 1/2004 | Koch et al. | 424/725 |
| 2005/0003026 A1 * | 1/2005 | Bok et al. | 424/736 |
| 2008/0206360 A1 * | 8/2008 | Hendrix | 424/682 |

OTHER PUBLICATIONS

Product for Sale: New Centrum Cardio. http://web.archive.org/web/20081002032838/http://www.centrum.com/product_detail.aspx?productid=CENTRUMCRDO&panel=tablets (2008).*
Unna et al. JPET Sep. 1942 vol. 76 No. 1 pp. 75-80, p. 77 last paragraph and p. 80 top paragraph.*
Powers. Am J. Clin Nurt Jun. 2003 vol. 77 No. 6 1353 left column paragraph 4.*

* cited by examiner

*Primary Examiner* — Anoop Singh
*Assistant Examiner* — Anna Falkowitz
(74) *Attorney, Agent, or Firm* — Salter & Michaelson

(57) ABSTRACT

A dietary supplement formulation for reducing the risk of coronary heart disease or stroke, and in which there is provided a plurality of vitamins and minerals that together represent a minimum daily requirement thereof. Added to this composition is aspirin and plant sterols.

10 Claims, No Drawings

COMPOSITION FOR CARDIOVASCULAR TREATMENT

FIELD OF THE INVENTION

The present invention relates to an improved formulation and composition for the treatment of heart attacks, strokes and other possible cardiovascular impediments. The present invention also pertains to an improved composition that combines certain effective components with daily minimum dosages of vitamins and minerals.

BACKGROUND OF THE INVENTION

At the present time there is no effective product on the market that combines a multivitamin and mineral formulation with effective means for treating cardiovascular impediments. Currently there are existing patents that address the use of aspirin (acetylsalicylic acid) to provide an improved vascular effect. For example, see the Finkelstein U.S. Pat. No. 7,202,229 that describes an aspirin formulation with quite limited vitamin usage. This particular patent combines aspirin with, for example, folic acid, arginine and garlic. Unfortunately, arginine has recently been shown to increase death in heart attack patients. Refer also to the Lesur et al. U.S. Pat. No. 5,998,448 for a showing of aspirin with limited vitamins. Refer also to the Heibel et al. U.S. Pat. No. 6,274,170 for a compound for cardiovascular treatment including aspirin.

In accordance with the present invention, the formulation is comprised of, not only aspirin and a multivitamin and minerals but also plant sterols. None of the above references teach this particular combination. This combination is effective in reducing the risk of coronary heart and artery disease.

Thus, in the prior art, there is no effective combination that includes aspirin, preferably in a relatively low dosage, a multivitamin and mineral combination, as well as plant sterols.

Accordingly, it is an object of the present invention to provide in a single dosage the required daily dosage of multivitamins and minerals along with the benefits of treating cardiovascular problems by the further incorporation of a low dosage of aspirin and plant sterols.

A further object of the present invention is to provide a composition that is not only effective in treating cardiovascular disease but also can be used in treating chronic headaches. In this regard, the Applicant wishes to incorporate by reference in its entirety its own co-pending application Ser. No. 12/465,030 filed on May 13, 2009. This co-pending application describes the use of a nutritional composition that replenishes any nutrients that may be lacking in the headache patient due to dietary restrictions or omissions.

As discussed in the background section of the co-pending application, currently available compositions that include co-enzyme Q-10, either alone or in combination with herbs, are limited to use for its antioxidant properties, and do not constitute a complete daily vitamin regime. In this regard refer, for example, to U.S. Pat. No. 6,465,517 to Van Der Zee for a composition for the treatment of migraine headaches. This patent describes the use of coenzyme Q-10, along with other components primarily for migraine headache relief, and including such additional components as creatine, L-carnitine, carbohydrates, proteins, fats and herbal extracts. Although this patent discloses a composition of coenzyme Q-10, because the emphasis is on migraine headache relief, there is no teaching of a complete daily multi-vitamin and mineral regime so as to address the patient's full nutritional needs. Accordingly, a further object of the present invention is to provide a composition that is effective, not only against cardiovascular effects but also for the treatment of headaches. In this regard, the composition of the present invention is readily administered with a single dosage. This dosage can be administered such as by one or more including, but not limited to, tablet, capsule, powder suspension, suppository, sustained release, buffered, liquid effervescent and enteric coated form.

SUMMARY OF THE INVENTION

To accomplish the foregoing and other objects, features and advantages of the present invention, there is provided a nutritional composition for treating cardiovascular disease by a combination of the required daily allowances of vitamins and minerals, in combination with low dosage aspirin and plant sterols. The composition is meant for application in a single dose. Preferably, the single dose is a single daily dose. The nutritional composition comprises a plurality of vitamins and a plurality of minerals that together represent at least a portion of required daily allowance thereof with the plurality of vitamins including at least vitamins A, C, D, E, K, B-1, B-2, B-6, and B-12, niacin, folic acid, biotin, pantothenic acid, and mixtures thereof, and the plurality of minerals including at least selenium, zinc, magnesium, calcium, iron, manganese, copper, chromium, phosphorous, iodine, potassium and molybdenum. The active ingredients include at least one or both of 125-175 mg of co-enzyme Q-10 and 25-150 mg of purified Butterbur root extract. The active ingredients include preferably both a low dosage amount of aspirin and a plant sterol.

In accordance with other aspects of the present invention the nutritional composition may include 10% to 100% of the required daily allowance (RDA) of each of the plurality of vitamins; 2% to 500% of the required daily allowance of each of the plurality of minerals; the magnesium and vitamin B-2 each being at least 400 mg; preferably on the order of 150 mg of co-enzyme Q-10; preferably in a range of aspirin of 25 mg to 325 mg and the plant sterols of at least 800 mg expressed as the weight of free phytosterols.

Also, in accordance with the present invention there is provided a composition for cardiovascular treatment by administering a daily dosage. The composition comprises about 5,000 I.U. of vitamin A, about 120 mg of Vitamin C, about 120 mg of Vitamin E (natural preferred), about 10 mg of Vitamin K, about 10 mg of Thiamin, about 10 mg of Riboflavin, about 40 mg of Niacin, about 4 mg of Vitamin B6, about 800 mcg of Folic Acid, about 200 mcg of Vitamin B12, about 300 mcg of Biotin, about 20 mg of Pantothenic Acid, about 200 mg of Calcium, about 8 mg of Iron, about 51 mg of Phosphorus, about 150 mcg of Iodine (from kelp/other nat'l source), about 400 mg of Magnesium, about 15 mg of Zinc, about 200 mg of Selenium, about 2 mg of Copper, about 2 mg of Manganese, about 200 mcg of Chromium, about 100 mcg of Molybdenum, and about 100 mg of Potassium.

DETAILED DESCRIPTION

The composition of the present invention combines a daily dose of vitamins and minerals with other active ingredients that together provide a dietary supplement formulation for the prevention of heart attack and stroke. The aforesaid active ingredients include aspirin and plant sterols. These are combined with the usual vitamins and minerals normally found in a daily multivitamin and mineral supplement.

The aspirin that is used is a low dose aspirin preferably on the order of 81 mg per dosage. Other possible dosages of aspirin can be 50 mg, 162 mg and 325 mg. The preferred maximum range of aspirin is 25 mg to 325 mg. As far as the plant sterols are concerned, these are to be provided in an amount of at least 800 mg expressed as the weight of free phytosterols.

The nutritional composition, in accordance with the present invention is for treating cardiovascular disease and in a preferred embodiment comprises a plurality of vitamins and a plurality of minerals that together represent at least a portion of required daily allowance thereof. The plurality of vitamins may include at least vitamins A, C, D, E, K, B-1, B-2, B-6, and B-12, niacin, folate, botin, pantothenic acid, and mixtures thereof. The plurality of minerals may include at least selenium, zinc, magnesium, calcium, iron, manganese, copper, chromium, cobalt, phosphorous, iodine, potassium, molybdenum, vanadium floride, chloride and silicon.

The nutritional composition may include 10% to 100% of the required daily allowance of each of the plurality of vitamins, and may include 2% to 500% of the required daily allowance of each of the plurality of minerals. In the nutritional composition the magnesium and vitamin B-2 are each at least 400 mg. This represents about 100% of the required daily allowance of magnesium and over 23,000% of the required daily allowance of vitamin B-2. The nutritional composition is applied by one or more of tablet, capsule, powder suspension, suppository, sustained release, buffered, liquid effervescent and enteric coated form. The following is a table that shows preferred amounts of the vitamins and minerals Also of importance is providing at least 400 mg of magnesium which represents about 100% of the RDA of magnesium, along with on the order of 400 mg of vitamin B-2 (riboflavin) which represents over 23,000% of the RDA of vitamin B-2.

The following is a list of vitamins and minerals that are preferred in accordance with the composition of the present invention, and including the preferred active ingredients for assisting in headache relief.

| Vitamin/Mineral Ingredients | Amount |
| --- | --- |
| Vitamin A (100% beta carotene) | About 5,000 I.U. |
| Vitamin C | About 120 mg |
| Vitamin E (natural preferred) | About 120 mg |
| Vitamin K | About 10 mg |
| Thiamin | About 10 mg |
| Riboflavin | About 10 mg |
| Niacin | About 40 mg |
| B6 | About 4 mg |
| Folic Acid | About 800 mcg |
| B12 | About 200 mcg |
| Biotin | About 300 mcg |
| Pantothenic Acid | About 20 mg |
| Calcium | About 200 mg |
| Iron | About 8 mg |
| Phosphorus | About 51 mg |
| Iodine (from kelp/other nat'l source) | About 150 mcg |
| Magnesium | About 400 mg |
| Zinc | About 15 mg |
| Selenium | About 200 mg (older adult prods range = 20-200 mcgs) |
| Copper | About 2 mg |
| Manganese | About 2 mg |
| Chromium | About 200 mcg |
| Molybdenum | About 100 mcg |
| Potassium | About 100 mg |
| Co-enzyme Q-10 | 125-175 mg |
| Butterbur root extract | 25-150 mg |

The following having now described the limited number of embodiments of the present invention, it should be apparent to those skilled in the art that numerous other embodiments and modifications thereof are contemplated as falling within the scope of the present invention as defined by the appended claims.

What is claimed is:

1. A dietary supplement formulation for reducing the risk of coronary heart disease or stroke, consisting of:
    a plurality of vitamins, excluding vitamin B2, and a plurality of minerals, excluding magnesium, that together represent a required daily allowance of 10% to 100% of the required daily allowance of vitamins, and 2% to 500% of the required daily allowance of minerals;
    said plurality of vitamins including vitamins A, C, D, E, B-1, B-6, and B-12, niacin, folate, botin, pantothenic acid, and mixtures thereof;
    said plurality of minerals including selenium, zinc, calcium, iron, manganese, copper, chromium, cobalt, phosphorous, iodine, potassium, chloride and silicon;
    aspirin (acetylsalicylic acid);
    plant sterols (phytosterols);
    wherein the aspirin is in a dosage range of 25 mg to 325 mg; wherein the plant sterols are expressed at the weight of free phytosterols, and the plant sterols are in a dosage of at least 800 mg expressed as the weight of free phytosterols; and
    including magnesium and vitamin B-2 each are at least 400 mg;
    co-enzyme Q-10 in a range of 125 to 175 mg; and
    Butterbur root extract in a range of 25 to 150 mg.

2. The dietary supplement formulation of claim 1 wherein the aspirin is in a dosage of around 82 mg.

3. The dietary supplement formulation of claim 1 wherein the aspirin is provided in any one of 50 mg, 81 mg, 162 mg and 325 mg.

4. The dietary supplement formulation of claim 1 wherein the composition is applied by one or more of tablet, capsule, powder suspension, suppository, sustained release, buffered, liquid effervescence, and enteric coated form.

5. The dietary supplement formulation of claim 1 wherein the formulation is for application in a single daily dose.

6. A composition for treating heart attacks and strokes consisting of:
    a plurality of vitamins, excluding vitamin B2, and a plurality of minerals, excluding magnesium, that together represent at least a portion of required daily allowance of 10% to 100% of the required daily allowance of vitamins, and 2% to 500% of the required daily allowance of minerals;
    said plurality of vitamins including vitamins A, C, D, E, K, B-1, B-6, and B-12, niacin, folate, botin, pantothenic acid, and mixtures thereof;
    said plurality of minerals including selenium, zinc, calcium, iron, manganese, copper, chromium, cobalt, phosphorous, iodine, potassium, molybdenum, vanadium floride, chloride and silicon;
    low dosage aspirin;
    a plant sterol;
    wherein the aspirin is in a dosage range of 25 mg to 325 mg; wherein the plant sterols are expressed at the weight of free phytosterols, and the plant sterols are in a dosage of at least 800 mg expressed as the weight of free phytosterols; and
    including magnesium and vitamin B-2 each are at least 400 mg;
    co-enzyme Q-10 in a range of 125 to 175 mg; and
    Butterbur root extract in a range of 25 to 150 mg.

7. The composition of claim 6 wherein the composition is applied by one or more of tablet, capsule, powder suspension, suppository, sustained release, buffered, liquid effervescent and enteric coated form.

8. The composition of claim 6 wherein the composition is administered in a single daily dose.

9. A composition for cardiovascular treatment by administering a daily dosage, the composition consisting of:
- about 5,000 I.U. of vitamin A;
- about 120 mg of Vitamin C
- about 120 mg of Vitamin E (natural preferred)
- about 10 mg of Vitamin K
- about 10 mg of Thiamin
- about 40 mg of Niacin
- about 4 mg of Vitamin B6
- about 800 mcg of Folic Acid
- about 300 mcg of Biotin
- about 20 mg of Pantothenic Acid
- about 200 mg of Calcium
- about 8 mg of Iron
- about 51 mg of Phosphorus
- about 150 mcg of Iodine (from kelp/other nat'l source)
- about 15 mg of Zinc
- about 200 mg of Selenium
- about 2 mg of Copper
- about 2 mg of Manganese
- about 200 mcg of Chromium
- about 100 mcg of Molybdenum
- about 100 mg of Potassium
- including magnesium and vitamin B-2 each are at least 400 mg
- aspirin in a dosage in a range of 25 mg to 325 mg;
- a plant sterol of at least 800 mg expressed as a weight of free phytosterols;
- co-enzyme Q-10 in a range of 125 to 175 mg; and
- Butterbur root extract in a range of 25 to 150 ma.

10. The composition of claim 9 wherein the composition is administered in a single daily dose.

* * * * *